United States Patent
Arrowood et al.

(10) Patent No.: US 9,067,845 B2
(45) Date of Patent: Jun. 30, 2015

(54) PROCESS FOR HYDROCHLORINATION OF MULTIHYDROXYLATED ALIPHATIC HYDROCARBONS

(75) Inventors: Tina L. Arrowood, Elko New Market, MN (US); William J. Kruper, Jr., Sanford, MI (US); John R. Briggs, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 250 days.

(21) Appl. No.: 13/697,038

(22) PCT Filed: May 19, 2011

(86) PCT No.: PCT/US2011/037129
§ 371 (c)(1),
(2), (4) Date: Nov. 9, 2012

(87) PCT Pub. No.: WO2011/149754
PCT Pub. Date: Dec. 1, 2011

(65) Prior Publication Data
US 2013/0066091 A1     Mar. 14, 2013

Related U.S. Application Data

(60) Provisional application No. 61/348,596, filed on May 26, 2010.

(51) Int. Cl.
*C07C 51/363* (2006.01)
*C07C 69/76* (2006.01)
(Continued)

(52) U.S. Cl.
CPC ............. *C07B 41/12* (2013.01); *C07C 29/62* (2013.01); *C07C 29/86* (2013.01); *C07C 67/11* (2013.01); *C07C 67/58* (2013.01); *C07C 67/08* (2013.01); *C07C 67/10* (2013.01)

(58) Field of Classification Search
CPC .. C07B 39/00; C07B 2200/07; C07C 51/363; C07C 17/02; C07C 29/66; C07C 51/60; C07C 67/24; C07C 69/76; C07C 69/78; C07C 67/08; C07C 405/00; C07C 2101/16; C07C 67/00; C08K 5/101; C11B 9/0034
USPC .................................. 554/159; 560/111, 231
See application file for complete search history.

(56) References Cited

U.S. PATENT DOCUMENTS

| | | | |
|---|---|---|---|
| 2,144,612 A | 1/1939 | Britton et al. | |
| 5,908,946 A | 6/1999 | Stern et al. | |

(Continued)

FOREIGN PATENT DOCUMENTS

| | | |
|---|---|---|
| FR | 2752242 | 2/1998 |
| FR | 2869612 | 11/2005 |

(Continued)

OTHER PUBLICATIONS

Process Economics Program Report 251, Biodiesel Production (Oct. 2004), (R.G. Bray, SRI Consulting, pp. 7-10 to 7-14).

*Primary Examiner* — Deborah D Carr

(57) ABSTRACT

A process for producing a chlorohydrin, an ester of a chlorohydrin, or a mixture thereof including the steps of contacting, in a hydrochlorination reactor, a multihydroxylated aliphatic hydrocarbon, an ester of a multihydroxylated aliphatic hydrocarbon, or a mixture thereof with a source of a hydrogen chloride, in the presence of a hydrophobic or extractable carboxylic acid catalyst is provided.

14 Claims, 1 Drawing Sheet

(51) Int. Cl.

| | |
|---|---|
| *C07C 69/02* | (2006.01) |
| *C07B 41/12* | (2006.01) |
| *C07C 29/62* | (2006.01) |
| *C07C 29/86* | (2006.01) |
| *C07C 67/11* | (2006.01) |
| *C07C 67/58* | (2006.01) |
| *C07C 67/08* | (2006.01) |
| *C07C 67/10* | (2006.01) |

(56) References Cited

U.S. PATENT DOCUMENTS

| | | |
|---|---|---|
| 7,151,187 B2 | 12/2006 | Delfort et al. |
| 7,268,192 B2 | 9/2007 | Asakage et al. |
| 7,732,627 B2 | 6/2010 | Takai et al. |
| 8,198,352 B2 | 6/2012 | Deelman et al. |
| 8,664,413 B2 | 3/2014 | Ishikawa et al. |
| 2005/0261509 A1 | 11/2005 | Delfort et al. |
| 2008/0015369 A1 | 1/2008 | Kruper, Jr. et al. |
| 2008/0015370 A1 | 1/2008 | Hook et al. |

FOREIGN PATENT DOCUMENTS

| | | |
|---|---|---|
| FR | 2869613 | 11/2005 |
| WO | 2006020234 | 2/2006 |
| WO | WO 2006020234 A1 * | 2/2006 |
| WO | 2008128013 | 10/2008 |

* cited by examiner

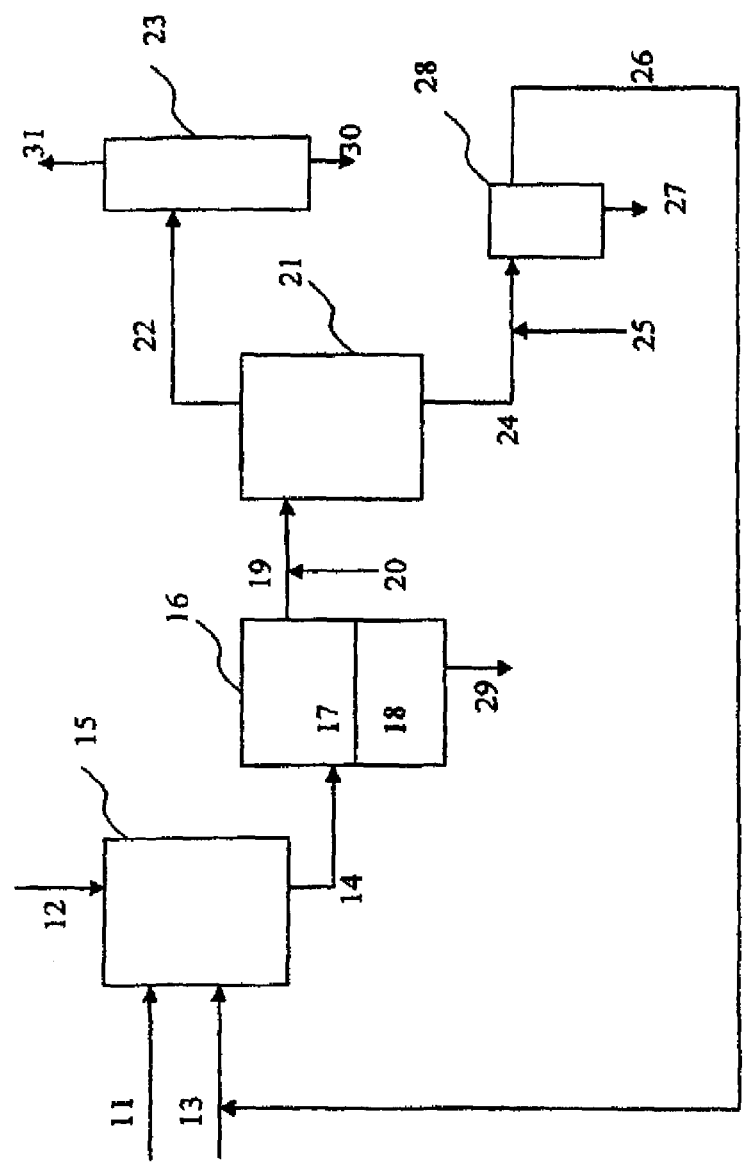

PROCESS FOR HYDROCHLORINATION OF MULTIHYDROXYLATED ALIPHATIC HYDROCARBONS

CROSS REFERENCE TO RELATED APPLICATIONS

This is a §371 application of PCT International Patent Application Number PCT/US11/037129 filed May 19, 2011, and claims priority from provisional application Ser. No. 61/348,596 filed May 26, 2010, each of which is incorporated herein by reference in its entirety.

FIELD OF THE INVENTION

The present invention relates to a process utilizing phase separation to recover chlorohydrin product formed in the hydrochlorination of multihydroxylated aliphatic hydrocarbons to chlorohydrins. More particularly, the present invention relates to a process for improving the conversion and facilitating product recovery of a multihydroxylated aliphatic hydrocarbon or mixtures of naturally derived multihydroxylated aliphatic hydrocarbons to a chlorohydrin in a process where the product may be separated from water by phase separation.

BACKGROUND OF THE INVENTION

Epichlorohydrin is a widely used precursor to epoxy resins. Epichlorohydrin is a monomer which is commonly used for the alkylation of para-bisphenol A; the resultant diepoxide, either as a free monomer or oligomeric diepoxide, may be advanced to high molecular weight resins which are used for example in electrical laminates, can coatings, automotive topcoats and clearcoats.

One known method to produce chlorohydrins as reactive intermediates in the manufacture of epoxies, is described in U.S. Pat. No. 2,144,612 in which glycerol (1,2,3-propanetriol, also known as glycerin or glycerine) is converted into an α-chlorohydrin by reaction with anhydrous hydrogen chloride (HCl) in the presence of a catalytic amount of acetic acid (AcOH). U.S. Pat. No. 2,144,612 describes a process that is shown in the following reaction sequence, shown in Scheme 1 below, for making epichlorohydrin via the reaction of glycerol with hydrogen chloride and acetic acid to make glycerol dichlorohydrin. As shown in Scheme 1, epichlorohydrin is produced from the glycerol dichlorohydrin by ring closure in the presence of caustic.

Scheme 1: Hydrochlorination of Glycerol

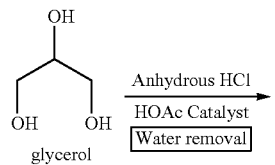

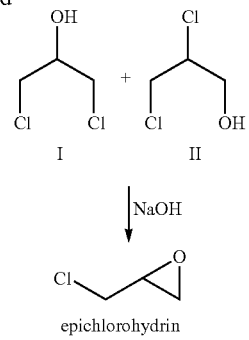

epichlorohydrin

Glycerol is considered to be a low-cost, renewable feedstock and is a co-product of the biodiesel process for making fuel additives. It is known that other renewable feedstocks such as fructose, glucose and sorbitol can be hydrogenolized to produce mixtures of diols and triols, such as glycerol, ethylene glycol, 1,2-propylene glycol, 1,3-propylene glycol and the like.

With abundant and low cost glycerol or mixed glycols, an economically attractive process for glycerol or mixed glycol hydrochlorination would be desirable. Hydrochlorination of multihydroxylated aliphatic hydrocarbons using HCl is an equilibrium-limited reaction in which water is produced. As the concentration of water builds in the product, the reaction rate declines and the conversion ultimately ceases.

Removal of water by evaporation, azeotropic distillation, reactive distillation or absorption into molecular sieves are known methods used to drive the hydrochlorination reaction further to the desired chlorohydrin product. Despite the considerable capital and processing costs of these water removal techniques, the reaction time for complete hydrochlorination remains greater than about 8 hours due to the inefficiency of these known methods of water removal.

Pending U.S. Patent Publication No. 20080015369 provides a process for producing a chlorohydrin, an ester of a chlorohydrin, or a mixture thereof comprising the step of contacting a crude glycerol an ester of a crude glycerol, or a mixture thereof with a source of a superatmospheric partial pressure of hydrogen chloride, in the presence of a catalyst to produce a chlorohydrin, an ester of a chlorohydrin, or a mixture thereof, said contacting step carried out without substantial removal of water; wherein said crude glycerol, said ester of crude glycerol, or mixture thereof is derived from a renewable raw material. "Superatmospheric pressure" herein means that the hydrogen chloride (HCl) partial pressure is above atmospheric pressure, i.e. 15 psia or greater.

It would be advantageous to further drive the hydrochlorination reaction to the desired chlorohydrin product, thereby decreasing the overall reaction time, by utilization of both superatmospheric conditions and water removal. However, removal of water by evaporation under superatmospheric conditions is not readily accomplished and use of absorption media is difficult to accomplish on an industrial scale.

It would, therefore, be an advance in the art of hydrochlorination chemistry to discover a simple and cost-effective method of transforming multihydroxylated aliphatic hydrocarbons to chlorohydrins (preferably with complete or substantially complete halogenation) under superatmospheric conditions during which water removal is accomplished during the hydrochlorination process by phase separation of the chlorohydrin ester.

SUMMARY OF THE INVENTION

One aspect of the invention is a process for producing a chlorohydrin, an ester of a chlorohydrin, or a mixture thereof comprising contacting, in a hydrochlorination reactor, a multihydroxylated aliphatic hydrocarbon, a multihydroxylated aliphatic hydrocarbon ester, or a mixture thereof with a source of hydrogen chloride, in the presence of a hydrophobic carboxylic acid catalyst to produce a first product stream comprising hydrophobic monochlorohydrin, hydrophobic dichlorohydrin, or a mixture thereof; recovering and phase separating the first product stream into a hydrophobic stream and a non-hydrophobic stream, wherein the non-hydrophobic stream comprises water and hydrogen chloride, and optionally unreacted multihydroxylated aliphatic hydrocarbon, unesterified monochlorohydrin and unesterified dichlorohydrin and the hydrophobic stream comprises the hydrophobic monochlorohydrin ester or diester, the hydrophobic dichlorohydrin ester, or the mixture thereof and the hydrophobic carboxylic acid catalyst; and decanting the hydrophobic stream to produce a chlorohydrin/catalyst stream.

Certain embodiments of the inventive process further comprise adding one or more strong bases including but not limited to strong bases selected from the group of lime, caustic potash and caustic soda, or mixtures thereof, to the chlorohydrin/catalyst stream to form a second product stream comprising epoxides, water, and the hydrophobic carboxylic acid and salt thereof; separating the second product stream into a stream comprising the epoxide and a stream comprising the hydrophobic carboxylic acid and salt thereof: adding a mineral acid to the stream comprising hydrophobic carboxylic acid salt to form a two phase mixture where one phase comprises the hydrophobic carboxylic acid and a second phase comprises water and a salt. The hydrophobic carboxylic acid phase is decanted and recycled to the hydrochlorination reactor.

Another aspect of the invention provides a process for producing a chlorohydrin, an ester of a chlorohydrin, or a mixture thereof consisting essentially of: contacting, in a hydrochlorination reactor, a multihydroxylated aliphatic hydrocarbon, a multihydroxylated aliphatic hydrocarbon ester, or a mixture thereof with a source of hydrogen chloride, in the presence of a hydrophobic carboxylic acid catalyst to produce a first product stream comprising hydrophobic monochlorohydrin ester or diester, hydrophobic dichlorohydrin ester, or a mixture thereof; recovering and phase separating the first product stream into a hydrophobic stream and a non-hydrophobic stream, wherein the non-hydrophobic stream comprises water and hydrogen chloride and the hydrophobic stream comprises the hydrophobic monochlorohydrin ester or diester, the hydrophobic dichlorohydrin ester, or the mixture thereof and the hydrophobic carboxylic acid catalyst; decanting the hydrophobic stream to produce a chlorohydrin/catalyst stream; adding caustic to the chlorohydrin/catalyst stream to form a second product stream comprising epoxides, water, and the hydrophobic carboxylic acid and salt thereof; separating the second product stream using evaporation to a stream comprising the epoxide and a stream comprising the carboxylic acid and the salt thereof; adding a mineral acid to the hydrophobic component to form a first recovery stream comprising hydrophobic carboxylic acid, water and a sodium salt; phase separating the first recovery stream to form a hydrophobic layer comprising hydrophobic carboxylic acid catalyst; and recycling the hydrophobic carboxylic acid catalyst to the hydrochlorination reactor.

In some embodiments, the hydrophobic carboxylic acid is one or more acids selected from the group consisting of benzoic acid, hexanoic acid, heptanoic acid, octanoic acid, oleic acid, stearic acid, terephthalic acid, phenylacetic acid. In alternative embodiments, the hydrophobic carboxylic acid is stearic acid, benzoic acid, heptanoic acid or octanoic acid.

In some embodiments involving extraction, the hydrophobic carboxylic acid is one or more acids selected from the group consisting of 4-aminophenylacetic acid, 4-aminobutyric acid, 4-dimethylaminobutyric acid, 6-aminocaproic acid, 4-aminophenylacetic acid, 4-hydroxyphenylacetic acid, glycolic acid, 4-dimethylaminobutyric acid, 4-trimethylammoniumbutyric acid, parahydroxybenzoic acid, methoxy, methoxy(ethoxy), and methoxy(ethoxyethoxy) acetic acids.

In some embodiments, the multihydroxylated aliphatic hydrocarbon is one or more multihydroxylated aliphatic hydrocarbon selected from the group consisting of 1,2-ethanediol; 1,2-propanediol; 1,3-propanediol; 1-chloro-2,3-propanediol; 2-chloro-1,3-propanediol; 1,4-butanediol; 1,5-pentanediol; 1,2-butanediol; 1,3-butanediol; 2,3-butanediol; 1,2-cyclohexanedimethanol; 1,2,3-propanetriol and mixtures thereof. In alternative embodiments, the multihydroxylated aliphatic hydrocarbon is glycerol or one or more glycols, or a mixture thereof. The multihydroxylated aliphatic hydrocarbon may be obtained from one or more renewable raw materials.

The inventive process utilizes a hydrogen chloride source which may be aqueous hydrogen chloride, hydrogen chloride in an organic solvent, hydrogen chloride gas at superatmospheric pressure, or anhydrous hydrogen chloride. In addition to anhydrous hydrogen chloride, this process also has the unexpected benefit of obtaining high chlorohydrin yields through the use of aqueous hydrogen chloride. Aqueous hydrochloric acid is an item of commerce which is readily transported and economically advantaged over anhydrous sources of hydrogen chloride.

In a specific aspect of the inventive process, the multihydroxylated aliphatic hydrocarbon, multihydroxylated aliphatic hydrocarbon ester, or mixture thereof is obtained from sugar hydrocracking, optionally in a polar solvent and the hydrophobic carboxylic acid catalyst is one or more $C_6$-$C_{30}$ carboxylic acids.

Another aspect of the invention is a process for producing a chlorohydrin, an ester of a chlorohydrin, or a mixture thereof comprising: contacting, in a hydrochlorination reactor, a multihydroxylated aliphatic hydrocarbon, a multihydroxylated aliphatic hydrocarbon ester, or a mixture thereof with a source of hydrogen chloride, in the presence of an extractable carboxylic acid catalyst to produce an extractable product stream comprising chlorohydrin esters and dichlorohydrin esters and, optionally, monochlorohydrins and dichlorohydrins, or a mixture thereof; adding an extraction medium to the extractable product stream; extracting into an extraction medium the monochlorohydrins, dichlorohydrins, chlorohydrin esters, or mixture thereof; and decanting the extraction medium containing the monochlorohydrins and dichlorohydrin esters, and optionally, chlorohydrins and dichlorohydrins, or mixture thereof. Some embodiments further comprise treating the decanted extraction medium by addition of a base to form epoxide, hydrolysis to liberate chlorohydrins, addition of an alcohol or mixture of alcohols to form transesters, or a combination thereof.

Yet another aspect of the invention is a product of the inventive process comprising a mixture of hydrophobic esters of ethylene chlorohydrin (2-chloroethanol), propylene chlorohydrin (1-chloropropan-2-ol, 2-chloropropan-1-ol, or a mixture thereof), and, optionally, dichlorohydrin (1,3-dichloropropan-2-ol, 2,3-dichloropropan-1-ol, or a mixture thereof), wherein the mixture comprises 10-40 wt % ethylene chlorohydrin hydrophobic ester, 20-80 wt % propylene chlorohydrin hydrophobic ester and 20-60 wt % dichlorohydrin hydrophobic ester.

BRIEF DESCRIPTION OF THE DRAWINGS

FIG. 1 is a process flowchart illustrating one embodiment of the process of the present invention.

DETAILED DESCRIPTION OF THE INVENTION

The term "multihydroxylated aliphatic hydrocarbon" means a hydrocarbon which contains at least two hydroxyl groups attached to separate saturated carbon atoms. The multihydroxylated aliphatic hydrocarbon may contain, but is not limited to, from 2 to about 60 carbon atoms. As used herein the term "multihydroxylated aliphatic hydrocarbon" includes compounds produced from a sugar.

The term "sugar" includes any carbohydrate or compound produced from a carbohydrate, including hydrates, dehydrated products, hydrogenated products, hydrocracking products, hydrolysis products, oxidation products, esters, ethers, hemiacetals, acetals, hemiketals, ketals, or materials that convert to sugars or derivatives under hydrolysis, hydrogenation or hydrocracking conditions; and mixtures thereof. Examples of sugars include, but are not limited to, mono- di-, tri-, oligo- and polysaccharides, starch, molasses, cellulose, hemicellulose, chitin, dextrose, sucrose, lactose, maltose, galactose, glucose, fructose, xylose, sorbitol, mannitol, xylitol, erythritol, thyritol, glycerol, and mixtures thereof.

The term "hydrophobic," as used herein, means repelling, tending not to combine with, or incapable of dissolving in water or other polar compounds.

As used herein, the term "hydrophobic carboxylic acid catalyst" means a carboxylic acid having a hydrophobic substituent group or a compound which can convert to a carboxylic acid having a hydrophobic substituent group ("hydrophobic carboxylic acid precursor") under hydrochlorination reaction conditions. Such convertible compounds include, for example, carboxylic acid halides, carboxylic acid anhydrides, carboxylic acid esters, carboxylic acid amides, carboxylic acid salt, nitriles, and mixtures thereof.

As used herein, the term "phase separation" means the separation of two or more liquid phases, including the separation of a substantially polar liquid phase from a substantially non-polar liquid phase and a substantially aqueous liquid phase from a substantially non-aqueous liquid phase.

One broad aspect of the invention provides a process of converting a multihydroxylated aliphatic hydrocarbon to a chlorohydrin comprising the step of contacting the multihydroxylated aliphatic hydrocarbon with a hydrogen chloride, source at superatmospheric partial pressure in the presences of a hydrophobic carboxylic acid catalyst, while at the same time providing substantial water removal, by phase separation.

Another broad aspect of the invention provides a process for converting a multihydroxylated aliphatic hydrocarbon to a chlorohydrin comprising the step of contacting the multihydroxylated aliphatic hydrocarbon with a hydrogen chloride source in the presence of a hydrophobic carboxylic acid, as a catalyst, to form hydrophobic chlorohydrin esters which phase separate from aqueous streams.

In some embodiments of the invention, the water removal method used in the invention does not involve reactive distillation, cryoscopic removal, azeotropic distillation, absorptive or evaporative methods. In alternative embodiments, water removal occurs by phase separation in conjunction with one or more of reactive distillation, cryoscopic removal, azeotropic distillation, absorptive or evaporative methods.

In one embodiment, a mixture of multihydroxylated aliphatic hydrocarbons obtained from sugar hydrocracking, optionally in a polar solvent, is subjected to hydrochlorination using a $C_6$-$C_{30}$ carboxylic acid catalyst, whereupon at least some of the resulting mixture of multihydroxylated aliphatic hydrocarbon chlorohydrin esters, before or after cooling, phase separate from the reaction solution and are recovered by decantation, or, optionally, extraction. In a subsequent step the mixture of multihydroxylated aliphatic hydrocarbon chlorohydrin esters may be treated with base to generate a mixture comprising epoxides and carboxylic acid and salt thereof. The epoxides are recovered from the process stream by any suitable process, including absorption, vaporization, extraction, or decantation. The carboxylate salt may be preferably recovered by any suitable means such as crystallization, adsorption, ion-exchange, or after acidification to the carboxylic acid by similar means, and including decantation of after phase separation, and recycled to the hydrochlorination process.

In another embodiment, a mixture of multihydroxylated aliphatic hydrocarbons obtained from sugar hydrocracking in water is subjected to hydrochlorination using a $C_6$-$C_{30}$ carboxylic acid catalyst. During or after hydrochlorination, the mixture of multihydroxylated aliphatic hydrocarbon chlorohydrin esters are phase separated from the polar phase, and recovered by decantation. This mixture is then treated with a mixture of the multihydroxylated aliphatic hydrocarbons obtained from sugar hydrocracking, and the liberated chlorohydrins are recovered by vaporization. The balance of the product stream may be recycled to the hydrochlorination reactor.

In yet another embodiment, a mixture of multihydroxylated aliphatic hydrocarbons obtained from sugar hydrocracking, optionally in a polar solvent, is subjected to hydrochlorination using a carboxylic acid catalyst which is insufficiently hydrophobic to phase separate from the product stream after hydrochlorination, but which can be extracted into an immiscible phase by extraction (an "extractable carboxylic acid catalyst") whereupon the mixture of multihydroxylated aliphatic hydrocarbon chlorohydrin esters in the extraction medium phase separate from the reaction solution and are recovered by decantation. This product may be converted to epoxide by treatment with base, hydrolyzed to liberate a mixture of chlorohydrins, or transesterified with an alcohol or mixture of alcohols, for example, a mixture of multihydroxylated aliphatic hydrocarbons obtained by sugar hydrocracking.

In another embodiment, a composition of a mixture of multihydroxylated aliphatic hydrocarbon chlorohydrin esters derived from hydrochlorination of the product of sugar hydrocracking which forms a separate liquid phase from water that includes hydrophobic esters of ethylene chlorohydrin (2-chloroethanol), propylene chlorohydrin (e.g. 1-chloropropan-2-ol, 2-chloropropan-l-ol, or mixture thereof), and optionally dichlorohydrin (e.g. 1,3-dichloropropan-2-ol, 2,3-dichloropropan-l-ol, or mixture thereof), or mixtures thereof.

Any single carbon of a multihydroxylated aliphatic hydrocarbon bearing the hydroxyl (OH) functional group must possess no more than one OH group, and must be sp3 hybridized. The carbon atom bearing the OH group may be primary, secondary or tertiary. The multihydroxylated aliphatic hydrocarbon used in the invention must contain at least two sp3 hybridized carbons each bearing an OH group. The multihydroxylated aliphatic hydrocarbon includes any vicinal-diol (1,2-diol) or triol (1,2,3-triol) containing hydrocarbon including higher orders of contiguous or vicinal repeat units. The definition of multihydroxylated aliphatic hydrocarbon also includes for example one or more 1,3-1,4-, 1,5- and 1,6-diol functional groups as well. The multihydroxylated aliphatic hydrocarbon may also be a polymer such as polyvinylalcohol. Geminal-diols, for example, would be precluded from this class of multihydroxylated aliphatic hydrocarbon compounds.

It is to be understood that the multihydroxylated aliphatic hydrocarbon can contain aromatic moieties or heteroatoms including for example halide, sulfur, phosphorus, nitrogen, oxygen, silicon, and boron heteroatoms; and mixtures thereof.

In the process according to the present invention, the multihydroxylated aliphatic hydrocarbon used can be a crude multihydroxylated aliphatic hydrocarbon product or a purified multihydroxylated aliphatic hydrocarbon product. A "crude" multihydroxylated aliphatic hydrocarbon product is a multihydroxylated aliphatic hydrocarbon which has not been submitted to any treatment after its manufacture. A "purified" multihydroxylated aliphatic hydrocarbon product is a multihydroxylated aliphatic hydrocarbon which has been submitted to at least one treatment after its manufacture. When the multihydroxylated aliphatic hydrocarbon is a crude product obtained from renewable raw materials, it can comprise, for example, water in addition to a metal salt. The metal salt is in particular a metal chloride, which is preferably chosen from NaCl and KCl. The metal salt can also be selected from metal sulfates such as sodium sulfate, potassium sulfate or mixtures thereof. The multihydroxylated aliphatic hydrocarbon used in some embodiments of the inventive process contains at least one solid or dissolved metal salt which is preferably selected from sodium chloride, potassium chloride, sodium sulfate, potassium sulfate or mixtures thereof. The same considerations apply to the ester of a multihydroxylated aliphatic hydrocarbon, or the mixture of the ester of a multihydroxylated aliphatic hydrocarbon and the multihydroxylated aliphatic hydrocarbon.

In an embodiment of the inventive process, the crude multihydroxylated aliphatic hydrocarbon product can also contain one or more organic compounds, such as carbonyl compounds, for example aldehydes, fatty acids, salts of fatty acids or esters of fatty acids, such as in particular mono- or polyesters of the multihydroxylated aliphatic hydrocarbon with fatty acid, optionally in combination with water. When the multihydroxylated aliphatic hydrocarbon is crude glycerol, the crude glycerol may contain fatty acids, wherein the fatty acids may be, in some embodiments saturated and unsaturated fatty acids containing more than 12 carbon atoms, for example, oleic, linoleic and linolenic acids. Acids such as stearic ($C_{18}$ saturated) and palmitic acid are also preferred examples of hydrophobic acids which can promote phase separated halohydrin formation. These acids are generally produced during the conversion of colza oil, palm oil, palm kernel oil, copra oil, babassu oil, rape oil, sunflower oil, corn oil, castor oil, cottonseed oil, peanut oil, soy oil, flaxseed oil, crambe oil, and all oils originating from, for example, any sunflower or rape plants obtained via genetic modification or hybridization; and combinations thereof by saponification, trans-esterification and hydrolysis reactions.

In addition, frying oils may be used in the present invention, as well as various animal oils, such as fish oils, tallow oil, lard oil, and oils obtained via quartering; and combinations thereof.

Among the oils useful in the present invention, are, for example partially modified oils via, for example, polymerization or oligomerization as is the case in "stand oils" of flaxseed oils, sunflower oils and blown vegetable oils; and mixtures thereof.

One particularly suitable glycerol useful in the present invention may be obtained during the transformation of animal fats. Another particularly suitable glycerol which may be used in the present invention, can be obtained during the production of oleochemicals or biodiesel. Still another suitable glycerol for use in the present invention can be obtained during the transformation of fats or oils—animal or vegetable—via trans-esterification in the presence of a heterogeneous catalyst, as described in French Patents 2752242; 2869612; and 2869613, each of which is incorporated herein by reference. In such process it may be advantageous to use a heterogeneous catalyst comprising mixed aluminum and zinc oxides, mixed zinc and titanium oxides, mixed zinc, titanium and aluminum oxides, and the mixed bismuth and aluminum oxides; and mixtures thereof. The heterogeneous catalyst may be operated in a fixed bed. This latter method, for example, can be a biodiesel production method.

Glycerol sourced from production of oleochemicals or biodiesel may be advantageously used in the present invention because of its lower cost when taken as crude glycerol, or when taken as un-neutralized crude glycerol. As described in "Process Economics Program Report 251, Biodiesel Production (October 2004), (R. G. Bray, SRI Consulting, pp. 7-10 to 7-14)", incorporated herein by reference, the alkaline catalyzed transesterification of oils or fats with alcohols to alkyl esters and glycerol results in a two phase mixture of alkaline-containing glycerol and alkyl esters. The crude mixtures of multihydroxylated-aliphatic hydrocarbons of the present invention may be used in any desirable non-limiting concentration. In general, higher concentrations are preferred for economic reasons. Useful concentrations for the multihydroxylated-aliphatic hydrocarbons of the present invention may include, for example from about 0.01 mole % to about 99.99 mole %, preferably from about 1 mole % to about 99.5 mole %, more preferably from about 5 mole % to about 99 mole %, and most preferably from about 10 mole % to about 95 mole %.

Likewise, the un-neutralized crude glycerol of the present invention may be used in any desirable non-limiting concentration. In general, higher concentrations are preferred for economic reasons. Useful concentrations for the un-neutralized crude glycerol of the present invention may include, for example, from about 0.01 mole % to about 99.99 mole %, preferably from about 1 mole % to about 99.5 mole %, more preferably from about 5 mole % to about 99 mole %, and most preferably from about 10 mole % to about 95 mole %. The composition of this un-neutralized crude glycerol may also include, for example, up to 10 mole % alkali metal, up to 30 mole % alkyl esters, up to 20% fatty acids or alkali salts of fatty acids, up to 50 mole % methanol, up to 50 mole % water.

In one embodiment of the process according to the present invention, the crude multihydroxylated aliphatic hydrocarbon product may generally comprise 40% or more by weight of the total multihydroxylated aliphatic hydrocarbon feed to the hydrochlorination reaction. In some instances, the crude product comprises at least 48% by weight or more of the total multihydroxylated aliphatic hydrocarbon feed; and alternatively, 73% or more by weight of the multihydroxylated aliphatic hydrocarbon.

Multihydroxylated aliphatic hydrocarbons useful in the present invention include for example 1,2-ethanediol; 1,2-propanediol; 1,3-propanediol; 3-chloro-1,2-propanediol; 2-chloro-1,3-propanediol; 1, 3-butanediol; 2,3-butanediol; 1,4-butanediol; 1,5-pentanediol; 1,2-butanediol; 1,2-cyclohexanedimethanol; 1,2,3-propanetriol (glycerol); and mixtures thereof. Preferably, the multihydroxylated aliphatic hydrocarbons used in the present invention include for example 1,2-ethanediol; 1,2-propanediol; 1,3-propanediol; 1-chloro-2,3-propanediol; 2-chloro-1,3-propanediol; and 1,2,3-propanetriol; with 1,2,3-propanetriol being most preferred.

The esters of a multihydroxylated aliphatic hydrocarbon can be present in the multihydroxylated aliphatic hydrocarbon and/or produced during the chlorohydrin production method and/or produced in advance of the chlorohydrin production method. Examples of esters of multihydroxylated aliphatic hydrocarbons useful in the present invention include for example ethylene glycol monooctanoate, propanediol monooctanoate, glycerol monooctanoate, glycerol monostearates, glycerol dioctanoate, glycerol distearate and mixtures thereof. In one embodiment, such esters can be made from mixtures of multihydroxylated aliphatic hydrocarbons with exhaustively esterified multihydroxylated aliphatic hydrocarbons, for example mixtures of glycerol trioctanoate and glycerol.

The multihydroxylated aliphatic hydrocarbon, the ester of a multihydroxylated aliphatic hydrocarbon, or the mixture thereof, according to the invention may be a crude multihydroxylated aliphatic hydrocarbon, the ester of a crude multihydroxylated aliphatic hydrocarbon, or the mixture thereof; and may be obtained from renewable raw materials or biomass.

"Renewable raw materials," herein means materials described in U.S. Patent Publication 20080015370, the disclosure of which is incorporated herein by reference, and includes starting materials for the inventive process which derive from renewable natural sources.

The term "chlorohydrin" herein means a compound containing at least one hydroxyl group and at least one chlorine atom attached to separate saturated carbon atoms. A chlorohydrin that contains at least two hydroxyl groups is also a multihydroxylated aliphatic hydrocarbon. Accordingly, the starting material and product of the present invention can each be chlorohydrins; in that case, the product chlorohydrin is more highly chlorinated than the starting chlorohydrin, i.e., has more chlorine atoms and fewer hydroxyl groups than the starting chlorohydrin. Some preferred chlorohydrins are chlorohydrins used, for example, as a starting material, or generated as an intermediate, and are, for example, 3-chloro-propane-1,2-diol, 2-chloro-propane-1,3-diol, and a combination thereof. A more preferred highly chlorinated chlorohydrin such as a dichlorohydrin, may be, for example, a product of the process of the present invention, including, for example, 2-chloroethanol, 1-chloropropane-2-ol, 2-chloropropane-1-ol, 3-chloropropane-1,2-diol, 2-chloropropane-1,3-diol, 1,3-dichloropropane-2-ol, 2,3-dichloropropane-1-ol, and combinations of at least two or more of these compounds.

The term "epoxide" is used to describe a compound containing one oxygen bridge on a carbon-carbon bond wherein the carbon atoms of the carbon-carbon bond are contiguous and the compound can include atoms other than carbon and oxygen atoms, such as hydrogen and halogens. Preferred epoxides are ethylene oxide, propylene oxide, butylene oxide, glycidol and epichlorohydrin.

Carboxylic acids, RCOOH, catalyze the hydrochlorination of multihydroxylated aliphatic hydrocarbons to chlorohydrins. The specific carboxylic acid catalyst chosen for a particular embodiment may be based upon a number of factors including for example, its efficacy as a catalyst, its cost, its stability to reaction conditions, and its physical properties, provided that the carboxylic acid is sufficiently hydrophobic to form a chlorohydrin ester that phase separates from, or can be extracted from, aqueous streams. The particular process, and process scheme in which the catalyst is to be employed may also be a factor in selecting the particular catalyst for the present process. The hydrocarbyl groups may be linear, branched or cyclic, and may be substituted or un-substituted or mixtures thereof. Permissible substituents include any functional group that does not detrimentally interfere with the performance of the catalyst, and may include heteroatoms. Non-limiting examples of permissible functional groups include chloride, bromide, iodide, hydroxyl, phenol, ether, amide, primary amine, secondary amine, tertiary amine, quaternary ammonium, sulfonate, sulfonic acid, phosphonate, and phosphonic acid or mixtures thereof, provided, however that the substituent group does not prevent the resultant chlorohydrin product from phase separating from an aqueous phase, and/or from being extracted from an aqueous phase.

The catalyst for the hydrochlorination reaction in embodiments of the invention (hydrophobic carboxylic acid catalysts, as defined above) are hydrophobic carboxylic acids and compounds which convert to a hydrophobic carboxylic acid under hydrochlorination reaction conditions. Hydrophobic carboxylic acids useful in the invention include, by way of example, benzoic acid, hexanoic acid, heptanoic acid, octanoic acid, oleic acid, stearic acid, terephthalic acid, phenylacetic acid or mixtures thereof. Additionally, materials that can be converted into hydrophobic carboxylic acids under hydrochlorination reaction conditions (hydrophobic carboxylic acid precursors), including for example carboxylic acid halides, carboxylic acid anhydrides, carboxylic acid esters, carboxylic acid amides, carboxylic acid salts and nitriles may also be used as hydrochlorination catalysts in embodiments of the invention or mixtures thereof. Hydrophobic carboxylic acid precursors useful in embodiments of the invention include, for example, benzoic anhydride, hexanoic acid chloride, heptanoic anhydride, octanoic anhydride, oleic anhydride, steric anhydride, benzoic acid chloride, hexanoic acid chloride, heptanoic acid chloride, octanoic acid chloride, phenyl acetate, hexyl acetate, heptyl acetate, octylacetate, or mixtures thereof. Mixtures of carboxylic acids may also be used in the present invention.

Alternative embodiments utilize a second class of hydrophobic carboxylic acids, namely hydrophobic carboxylic acids that give esters having a distribution coefficient of ≥b1.1, wherein the distribution coefficient is defined as concentration in the non-polar phase/concentration in the polar phase. Such second class of hydrophobic carboxylic acids may be optimally used when extraction is used, and include, for example, 4-aminophenylacetic acid, 4-aminobutyric acid, 4-dimethylaminobutyric acid, 6-aminocaproic acid, 4-aminophenylacetic acid, 4-hydroxyphenylacetic acid, glycolic acid, 4-dimethylaminobutyric acid, 4-trimethylammoniumbutyric acid, parahydroxybenzoic acid, methoxy, methoxy (ethoxy), and methoxy(ethoxyethoxy) acetic acids.

A preferred hydrophobic carboxylic acid for use in embodiments of the invention is an acid with a $C_6$-$C_{18}$ hydrocarbyl group, or mixtures thereof, wherein this moiety is not sterically hindering the carboxylic acid group. Preferred acids for use in the inventive process are hexanoic acid, benzoic acid, octanoic acid and mixtures thereof.

The hydrogen chloride source used in the present invention is preferably introduced as a gas, a liquid or in a solution or a mixture, or a mixture thereof, such as for example a mixture of hydrogen chloride and nitrogen gas, so long as the required partial pressures of the hydrogen chloride are provided for the process of the present invention.

Alternative hydrogen chloride sources include hydrogen chloride gas, aqueous HCl, anhydrous HCl and any form of hydrogen chloride solubilized in an organic solvent. Common hydrogen chloride solvents include, but are not limited to diethylether, dioxane, methanol and ethanol and mixtures thereof. In those aspects of the invention which are operated under superatmospheric conditions the source of chloride must generate the required partial pressure of hydrogen chloride. Chloride in particular may be introduced with any number of cations including those associated with phase transfer reagents such as quaternary ammonium and phosphonium salts (for example tetra-butylphosphonium chloride) or mixtures thereof. Alternatively, ionic liquids such n-butyl-2-methylimidazolium chloride may be used as a synergist to promote the acid catalyzed displacement of OH from the multihydroxylated aliphatic hydrocarbon.

It is also known that these other halide sources may act as co-catalysts for the hydrochlorination of alcohols. In this respect catalytic amounts of iodide or bromide may be used to accelerate these reactions. These reagents may be introduced as gases, liquids or as counterion salts using a phase transfer or ionic liquid format. The reagents may also be introduced as metal salts wherein the alkali or transition metal counterion does not promote oxidation of the multihydroxylated aliphatic hydrocarbon. Care must be employed in using these co-catalysts in controlled hydrochlorination processes because the potential for formation of undesired chlorinated compounds may increase. Mixtures of different sources of halide may be employed, for example hydrogen chloride gas and an ionic chloride, such as tetraalkylammonium chloride or a metal halide. For example, the metal halide may be sodium chloride, potassium iodide, potassium bromide and the like or mixtures thereof.

In some embodiments of the invention utilizing superatmospheric partial pressure of HCl conditions, preferred hydrophobic carboxylic acid catalysts used in the present invention include for example benzoic acid, hexanoic acid, heptanoic acid, octanoic acid oleic acid, steric acid, 6-chlorohexanoic acid, and mixtures thereof.

In another embodiment of the present invention, some of the catalysts of the present invention that work in the superatmospheric pressure process described above may also work surprisingly well at atmospheric and subatmospheric pressure conditions with water removal by phase separation. Accordingly, one embodiment of the present invention is directed to a process for producing a chlorohydrin, an ester of a chlorohydrin, or a mixture thereof comprising the step of contacting a multihydroxylated aliphatic hydrocarbon, an ester of a multihydroxylated aliphatic hydrocarbon, or a mixture thereof with a source of a superatmospheric, atmospheric, or subatmospheric partial pressure of hydrogen chloride to produce a chlorohydrin, an ester of a chlorohydrin, or a mixture thereof, in the presence of a catalyst, wherein the catalyst (i) is a hydrophobic carboxylate derivative having six or more carbon atoms. In accordance with this embodiment of the present invention, the certain catalysts may also be advantageously employed at superatmospheric, atmospheric or sub-atmospheric pressure, and particularly in circumstances where an aqueous phase is continuously or periodically removed from the reaction mixture by phase separation. For example, the hydrochlorination of glycerol reaction can be practiced by sparging hydrogen chloride gas through a mixture of a multihydroxylated aliphatic hydrocarbon and a hydrophobic carboxylic acid catalyst.

The preferred hydrophobic carboxylic acid catalyst concentrations in the hydrochlorination step are, for example at least about 20 mole % based upon the moles of multihydroxylated aliphatic hydrocarbon, more preferably from about 50 mole % to about 200 mole %, more preferably from about 80 mole % to about 120 mole % and most preferably from about 90 mole % to about 110 mole %. The specific concentration of hydrophobic carboxylic acid catalyst employed may depend upon the specific catalyst employed and the process scheme in which such catalyst is employed.

In some embodiments of the invention, the process is carried out under superatmospheric pressure conditions. "Superatmospheric pressure" herein means that the hydrogen chloride (HCl) partial pressure is above atmospheric pressure, i.e. 15 psia or greater. Generally, the hydrogen chloride partial pressure employed in the inventive process is at least about 15 psia HCl or greater. Preferably, the pressure of the inventive process is not less than about 25 psia, more preferably not less than about 50 psia HCl, and most preferably not less than about 75 psia; and preferably not greater than about 1000 psia HCl, more preferably not greater than about 600 psia, and most preferably not greater than about 151 psia.

The HCl used in some embodiments of the invention is anhydrous. In alternative embodiments of the invention, aqueous HCl is used, including for example, 6M HCl, more preferably 12M HCl. The HCl concentration in the aqueous solution can range from less than 100 weight % hydrogen chloride to about 15 weight % hydrogen chloride. Preferably, the HCl concentration is greater than about 15 weight % HCl, more preferably about 35 weight % HCl.

The temperatures useful in the practice of the inventive process are sufficient to give economical reaction rates, but not so high that starting material, product or catalyst stability become compromised. Furthermore, high temperatures increase the rate of undesirable uncatalyzed reactions, such as non-selective over-chlorination, and can result in increased rates of equipment corrosion. Useful temperatures in the inventive process generally may be from about 25° C. to 300° C., alternatively from about 25° C. to about 200° C., alternatively from about 30° C. to about 160° C., alternatively from about 40° C. to about 150° C., and alternatively from about 50° C. to about 140° C.

The reaction of the superatmospheric pressure process of the present invention is advantageously rapid and may be carried out for a time period of less than about 12 hours, preferably less than about 5 hours, more preferably less than about 3 hours and most preferably less than about 2 hours.

In the superatmospheric pressure process of the present invention, it is also not necessary to use starting materials that are free of contaminants such as water, salts or organic impurities other than multihydroxylated aliphatic hydrocarbons. Accordingly, the starting materials may contain, generally, no more than about 50 weight percent of such contaminants. For example, a crude 1,2,3-propanetriol (i.e., crude glycerol, neutralized or unneutralized) that may contain certain impurities may be used in the process of the present invention. For example the crude glycerol useful in the present invention may contain up to 25% by weight water, up to 20% by weight inorganic salts, and up to about 25% by weight organic compounds other than glycerol. In another embodiment, a crude glycerol (neutralized or unneutralized) that may contain water (from about 0.05% to about 25% weight percent), alkali (for example, sodium or potassium) or alkaline earth (for example, calcium or magnesium) metal salts (from about 0.01% to about 20% by weight), alkali carboxylate salts (from about 0.01% to about 5% by weight), and/or organic compounds other than glycerol (from about 0.01% to about 25% weight percent) can also be used in the present invention effectively to produce the desired product. In still another embodiment, the crude glycerol (neutralized or unneutralized) preferably contains less than about 25 weight % water, less than about 25 weight % alkali or alkaline earth metal salts and less than about 25% organic compounds other than glycerol, where the total impurities comprise less than about 50% of the total. More preferably, the crude glycerol (neutralized or unneutralized) contains less than about 15 weight % water, less than about 20 weight % alkali or alkaline earth metal salts and less than about 5% organic compounds other than glycerol. And even more preferably, the crude glycerol (neutralized or unneutralized) contains less than about 10 weight % water, less than about 0.1 weight % alkali or alkaline earth metal salts, and less than about 0.1% organic compounds other than glycerol. Most preferably, the crude glycerol (neutralized or unneutralized) may be partially refined to contains less than about 10 weight % water, less than about 0.1 weight % alkali or alkaline earth metal salts, and less than about 0.1 weight % organic compounds other than glycerol. Consequently, the inventive process is a particularly economical approach.

The present invention may include various process schemes, including for example batch, semi-batch, or continuous. In one embodiment, for example, the present invention includes the hydrochlorination of a multihydroxylated aliphatic hydrocarbon by reaction with hydrogen chloride using a hydrophobic carboxylic acid catalyst. The multihydroxylated aliphatic hydrocarbon may be employed neat or diluted in an appropriate solvent. Such solvents may include for example water and alcohols. It may be preferred to purify the multihydroxylated aliphatic hydrocarbon before it is employed in the hydrochlorination reaction by removing contaminants, including water, organic materials or inorganic materials before use. This purification may include well known purification techniques such as distillation, extraction, absorption, centrifugation, or other appropriate methods. The multihydroxylated aliphatic hydrocarbon is generally fed to the process as a liquid although this is not absolutely necessary.

The hydrogen chloride employed in the process is preferably gaseous. The hydrogen chloride may, however, be diluted in a solvent such as an alcohol (or water) (for example methanol); or in a carrier gas such as nitrogen, if desired. Optionally, the hydrogen chloride may be purified before use to remove any undesirable contaminants. It is preferred that the hydrogen chloride be substantially anhydrous although some amounts (for example less than about 50 mole %, preferably less than about 20 mole %, more preferably less than about 10 mole %, even more preferably less than about 5 mole %, most preferably less than about 3 mole %) of water present in the hydrogen chloride are not excessively detrimental. The hydrogen chloride is fed to the process equipment in any suitable manner. It is preferred that the process equipment is designed to ensure good dispersal of the hydrogen chloride throughout the hydrochlorination reactor that is employed in the present process. Therefore, single or multiple spargers, baffles and efficient stirring mechanisms are desirable.

The catalyst employed may be fed to the process equipment independently, or as a mixture with, or component of, the multihydroxylated aliphatic hydrocarbon or hydrogen chloride feeds.

The equipment useful for the hydrochlorination reaction may be any well-known equipment in the art and should be capable of containing the reaction mixture at the conditions of the hydrochlorination. Suitable equipment may be fabricated of materials which are resistant to corrosion by the process components, and may include for example, metals, such as tantalum, suitable metallic alloys such as Hastelloy® C, or glass-lined equipment. Suitable equipment may include, for example, single or multiple stirred tanks, tubes or pipes, or combinations thereof.

In an exemplifying batch process, the multihydroxylated aliphatic hydrocarbon and hydrochlorination catalyst are charged to a pressure reactor. Hydrogen chloride aqueous solution is added to the reactor and the reactor heated to achieve the desired pressure for the desired length of time. The reactor contents are then discharged from the reactor and either purified or sent to other equipment for further processing, or to storage.

In an illustrative semi-batch process, one or more of the reagents is fed to a reactor over a period of time throughout the reaction while other reagents are fed only at the start of the reaction. In such a process, for example, the multihydroxylated aliphatic hydrocarbon and catalyst may be fed in a single batch to a hydrochlorination reactor, which is then held at reaction conditions for a suitable time, while hydrogen chloride is fed continuously throughout the reaction at the desired rate, which may be at constant flow, or constant pressure. After the reaction, the hydrogen chloride feed can be terminated and the reactor contents may be discharged for storage, purification or further processing.

In the large-scale production of chemicals it is often desirable to employ a continuous process since the economic advantage of doing so is usually greater than for batch processing. The continuous process may be, for example, a single-pass or a recycle process. In a single-pass process, one or more of the reagents pass through the process equipment once, and then the resulting effluent from the reactor is sent for purification or further processing. In such a scheme, the multihydroxylated aliphatic hydrocarbon and catalyst may be fed to the equipment and hydrogen chloride added as desired at a single point or at multiple points throughout the process equipment, which may include continuous stirred tank reactors, tubes, pipes or combinations thereof.

The reagents and catalysts are fed at such a rate that the residence time in the process equipment is appropriate to achieve a desired conversion of the multihydroxylated aliphatic hydrocarbon to products. The material exiting the process equipment is sent to storage, or to purification or further processing, as desired. In such a process, it is generally desirable to convert as much multihydroxylated aliphatic hydrocarbon to desired product as possible.

In a continuous recycle process, one or more of the unreacted multihydroxylated aliphatic hydrocarbon, reaction intermediates, hydrogen chloride, or catalyst exiting from the process equipment are recycled back to a point earlier in the process. In this manner, raw material efficiencies are maximized or catalysts reused. Thus, it is desirable to provide a means for removing such impurities from the process.

Removal of the desired hydrophobic chlorohydrin product from the aqueous process components can be achieved in a variety of ways. However, due to the hydrophobicity of the chlorohydrin product and the catalyst, recovery of the hydrophobic chlorohydrin and catalyst may be achieved by simple phase separation and decanting.

Subsequent epoxidation of the chlorohydrin results in a reaction product from which the epoxide (e.g., epichlorohydrin) may be separated from the hydrophobic carboxylic acid catalyst by any known or unknown means including distillation, vaporization, decantation, extraction or a combination thereof as is known in the art. The aqueous stream containing the catalyst and caustic may then be acid treated to form an aqueous sodium salt layer and an organic catalyst containing layer. The catalyst is then preferably recycled to the hydrochlorination reactor.

The particular process scheme employed may depend upon many factors including, for example, the identity, cost and purity of the multihydroxylated aliphatic hydrocarbon being hydrochlorinated, the specific process conditions employed, the separations required to purify the product, and other factors. The examples of processes described herein are not to be considered as limiting the present invention.

FIG. 1 illustrates a non-limiting embodiment of the invention. FIG. 1, for example, shows a process of the present invention wherein a multihydroxylated aliphatic hydrocarbon such as a glycerol feed stream, 11, is introduced into a hydrochlorination vessel, 15. The hydrochlorination vessel 15, may be of any well-known suitable type, including for example, one or more continuous stirred tank reactors (CSTRs) or tubular reactors; or combinations thereof. Also introduced to hydrochlorination vessel 15, are a hydrogen chloride feed stream, 12 and a hydrophobic carboxylic acid catalyst 13. Stream 11 and 13 may be fed into hydrochlorination vessel 15 either separately or together. Streams 11 and 12 may be fed into hydrochlorination vessel 15 either separately or together. Streams 12 and 13 may be fed into hydrochlorination vessel 15 either separately or together. In addition, optionally, all of the streams 11, 12, and 13 may be combined together into one feed stream. Any of the streams 11, 12, or 13, may be introduced at a single point or at multiple points of hydrochlorination vessel 15.

In hydrochlorination vessel 15, glycerol is partially or fully converted to its esters, monochlorohydrins and dichlorohydrins and their esters with the hydrophobic carboxylic acid catalyst. Any of the streams 11, 12, or 13 may optionally include recycled materials. Stream 14, containing, for example dichlorohydrins, monochlorohydrins, unreacted glycerol, and their esters, water, unreacted hydrogen chloride and catalyst exits hydrochlorination vessel 15, and enters vessel 16 in which non-hydrophobic stream 18 and hydrophobic stream 17 separate. Non-hydrophobic stream 18 comprises water, unreacted multihydroxylated aliphatic hydrocarbon, non-hydrophobic monochlorohydrins and hydrogen chloride and may exit vessel 16 through line 29. Hydrophobic stream 17 comprises hydrophobic carboxylic acid, hydrophobic chlorohydrin esters, including hydrophobic dichlorohydrins and hydrophobic monochlorohydrins. Hydrophobic stream 17 is passed from vessel 16 through line 19 into vessel 21. A strong base, such as caustic, 20 may be co-fed through line 19 into vessel 21 (as shown in FIG. 1) or separately added (not shown) to vessel 21.

In vessel 21, the strong base and chlorohydrin esters react to form an epoxide, such as epichlorohydrin. A mixture 22 of the epoxide, e.g. epichlorohydrin, and water may be separated from other epoxidation by-products and unreacted reagants by any known or unknown means including distillation, vaporization, decantation, extraction or a combination thereof as is known in the art. Following separation, the mixture 22 of epoxide, such as epichlorohydrin and water may be removed from vessel 21 and subsequently sent to storage or for separation. In FIG. 1, a separation vessel 23 is shown. The epoxide 30 may be separated from water 31 in vessel 23 by any of a number of known methods. Stream 24 containing hydrophobic catalyst and water, and water soluble or heavy impurities may be removed from vessel 21. Stream 24 may optionally be treated with a strong acid, e.g. aqueous hydrogen chloride, shown as stream 25 in FIG. 1, to cause the formation of an aqueous salt stream 27 which may be separated from the hydrophobic catalyst 26 in vessel 28. The hydrophobic catalyst stream 26 may be recycled for multihydroxylated aliphatic hydrocarbon hydrochlorination directly to vessel 15, or optionally combined with stream 13 (as shown in FIG. 1). Stream 24 may alternatively be added to the hydrochlorination vessel 15 directly without treatment with a strong acid.

Hydrochlorination vessel 15 may comprise any known suitable reaction vessel, including, for example, one or more stirred tank reactors, tubular reactors, bubble column reactors, and/or trickle bed reactors.

Vessels 16 and 28 may comprise any well-known suitable separation vessel, including, for example, one or more decanters, centrifuges, and/or Karr columns Vessel 21 may comprise any known suitable combined reaction and separation vessel or vessels, including one or more stirred tank reactors, tubular reactors, bubble column reactors, trickle bed reactors, and/or reactive distillation column reactors.

The following examples are for illustrative purposes only and are not intended to limit the scope of the present invention.

EXAMPLE 1

Preparation of a Chlorohydrin from Glycerol

Glycerol (15 g, 0.163 mol, obtained from Sigma-Aldrich Chemical Corporation) and benzoic acid (19.9 g, 0.163 mol, obtained from Sigma-Aldrich Co.) were added to a 100 mL Hastelloy® C Parr reactor (available from Parr Instrument Company) equipped with a Magnedrive stirrer, internal cooling coils, and a thermocouple. The reactor was sealed, pressurized to 100 psig and heated to 100° C. Anhydrous hydrogen chloride gas (from BOC Gases) was continuously fed to the reactor to maintain a pressure of 100 psig. After 2 hours, the reactor was allowed to cool to about 25° C., the reactor was vented to a caustic scrubber and the reactor contents were discharged. The reactor contents (44.7 g) were collected. Two liquid layers and a solid were present in the recovered contents. The top liquid layer (10 g) was analyzed by gas chromatography (GC) using a 30 meter Restek-35 capillary GC column and a flame ionization detector (FID) and found to be predominantly water with a trace amount of glycerol. The bottom liquid layer (28.3 g) was sampled and dissolved in deuterated methanol (MeOD) [obtained from Sigma-Aldrich Co.]. Then the sample was analyzed by $^1$H NMR using a Varian 300 MHz NMR instrument. The bottom liquid layer was 1,3 dichlorohydrin benzoate with trace amounts of benzoic acid. The solid (1.96 g isolated by filtration) was analyzed using a Varian 300 MHz instrument and MeOD solvent; and was found to be benzoic acid.

EXAMPLE 2

Preparation of a Chlorohydrin from Glycols

A mixture of ethylene glycol (EG) (5 g, 0.08 1 mol, obtained from Aldrich), propylene glycol (PG) (5 g, 0.066 mol, obtained from Aldrich), water (10 g, 0.555 mol), and octanoic acid (21.1 g, 0.1464 mol, obtained from Aldrich) were added to a 100 mL Hastelloy® C Parr reactor equipped with an HCl feed system, a mechanical stirrer, and temperature and pressure control systems. The reactor was sealed and the contents were heated to 100° C.; and then anhydrous HCl gas (obtained from BOC Gases) was added to the reactor to achieve and maintain a reactor pressure of 100 psig. After 3 hours, the HCl feed was terminated and the reactor was allowed to cool to about 25° C. Residual HCl pressure was vented through a caustic scrubbing system before the reactor contents were discharged. Two liquid phases from the reactor were recovered. Each phase was analyzed by GC using a 30 meter Restek-35 capillary GC column and an FID detector for composition. The results of the analysis are given in Table 1.

TABLE 1

|  | Top Layer Wt % | Bottom Layer Wt % |
|---|---|---|
| 1-chloro-2-propanol | 1.5 | 5.89 |
| 2-chloro-1-propanol | nd | 0.68 |
| chloroethanol | 0.77 | 5.02 |
| 1-chloropropan-2-yl octanoate | 27.8 | 0.94 |
| 2-chloropropyl octanoate | 7.09 | 0.35 |
| Chloroethyl octanoate | 40.84 | 1.45 |
| Unidentified* | nd | 0.46 |
| Octanoic acid | 24.61 | 1.078 |
| Water (by difference) | 0 | 84 |

*The unidentified component exhibited a retention time of 11.910 min.

The top layer of the reactor contents was decanted and washed twice with a saturated solution of sodium bicarbonate and twice with water resulting in a pH neutral organic layer. The organic layer was placed into a three necked round bottom flask fitted with a magnetic Teflon® (Teflon is a registered mark of E. I. du Pont de Nemours and Company Corporation) stir bar, an in-process temperature indicator, a nitrogen gas inlet and a glass transfer line to a dry ice/acetone cooled receiving flask with a nitrogen gas outlet. The reaction flask was heated to 50° C. using an oil bath and 5% NaOH (2 mole equivalents with respect to the chlorohydrin esters) in water was slowly added to maintain a reaction temperature of 50° C. The reaction mixture was maintained at that temperature for 2.5 hours at which time a single phase was observed in the reaction flask. The products collected in the cool receiving flask were identified to be primarily ethylene oxide and propylene oxide, with trace amount of water, by dissolving in MeOD and analyzing by 1H NMR using a Varian 300 MHz instrument. Concentrated HCl was added to the reaction flask until an acidic pH was obtained resulting in two phases. GC analysis of the bottom aqueous layer using a Restek-35 column and a FID detector indicated a composition comprising 0.2 wt % ethylene glycol, 0.3 wt % propylene glycol and 0.08 wt % octanoic acid. Only octanoic acid was detected in the upper layer by GC analysis using a Restek-35 column and a FID detector; therefore, most of the octanoic acid partitioned to the upper layer.

EXAMPLE 3

Hydrochlorination of Glycols

A mixture of ethylene glycol (2 g, 0.032 mol), propylene glycol (2 g, 0.026 mol), and octanoic acid (8.35 g, 0.058 mol) were added to 30 ml of 12M aqueous HCl in a 100 ml Hastelloy® C Parr reactor. The reactor was sealed and heated to 120° C. with no additional HCl added. After 4 hours, the reactor was cooled, vented, and the contents discharged. Two liquid layers were recovered—a top layer (9.1 g) and a bottom layer (36.47 g). GC analysis was conducted on each layer and the results are shown in Table 2.

TABLE 2

|  | Top Layer | | | Bottom Layer | | |
|---|---|---|---|---|---|---|
|  | wt % | grams | mmol | wt % | grams | mmol |
| Chloroethanol | 0.489 | 0.045 | 0.5 | 3.3 | 1.20 | 15 |
| 1-chloropropanol | 0.7 | 0.064 | 0.6 | 2.59 | 0.94 | 10 |
| 2-chloropropanol | 0.25 | 0.023 | 0.2 | 0.67 | 0.24 | 2.5 |
| Ethylene glycol | nd | | | | | |
| Propylene glycol | nd | | | | | |
| Octanoic acid | 55.5 | 5.056 | 3.5 | 2.33 | 0.85 | 5.9 |
| Chloroethyl octanoate | 25.04 | 2.281 | 11.1 | 1.08 | 0.39 | 1.9 |
| 1-chloropropan-2-yl octanoate | 11.67 | 1.063 | 4.8 | 0.52 | 0.19 | 0.86 |
| 2-chloropropyl octanoate | 5.9 | 0.537 | 2.5 | 0.31 | 0.11 | 0.51 |

The resulting material balance for ethylene glycol was 32 mmol input and 28.5 mmol output; and for propylene glycol was 26 mmol input and 22 mmol output.

EXAMPLE 4

Measurement of Distribution Coefficients 1,3-Dichlorohydrin esters of acetic aid, benzoic acid and hexanoic acid were synthesized. Each of the esters were mixed separately with 1-chloropropane-2,3-diol and glycerol. After vigorous mixing, the samples were allowed to stand for at least 30 minutes at a given temperature. Where two phases were observed to separate, the phases were analyzed by gas chromatography. The compositions of the phases are shown in Table 3.

TABLE 3

| 1,3-Dichlorohydrin Ester | Polar Phase | Temperature | Compositions | | | |
|---|---|---|---|---|---|---|
|  |  |  | Upper Layer | | Lower Layer | |
|  |  |  | Ester | Polar | Ester | Polar |
| Hexanoate | Glycerol | 100 | 98.9 | 1.1 | 0.25 | 99.75 |
| Hexanoate | Glycerol | 50 | 97.8 | 2.2 | 0.5 | 00.5 |
| Hexanoate | MCH** | 100 | No phase separation | | | |
| Hexanoate | MCH | 50 | | | | |
| Hexanoate | MCH | 30 | 85.5 | 14.5 | 20.0 | 80.0 |
| Benzoate | Glycerol | 100 | 98.5 | 2.5 | 3.3 | 96.7 |
| Benzoate | MCH | 100 | No phase separation | | | |
| Benzoate | MCH | 30 | | | | |
| Acetate | Glycerol | 105 | 100 | 0 | 1.0 | 99.0 |
| Acetate | Glycerol | 50 | 97.8 | 2.2 | 0.5 | 99.5 |
| Acetate | MCH | 100 | No phase separation | | | |
| Acetate | MCH | 30 | | | | |

**1-chloro-2,3-propanediol.

As an be seen from Table 3, the pure ester will phase separate from glycerol in each case, but only the more hydrophobic hexanoic ester will phase separate from pure MCH (monochlorohydrin).

The invention claimed is:

1. A process for producing a chlorohydrin, an ester of a chlorohydrin, or a mixture thereof comprising the steps of:
    (a) contacting, in a hydrochlorination reactor, a multihydroxylated aliphatic hydrocarbon, a multihydroxylated aliphatic hydrocarbon ester, or a mixture thereof with a source of hydrogen chloride, in the presence of a hydrophobic carboxylic acid catalyst to produce a first product stream comprising chlorohydrins, hydrophobic chlorohydrin esters, or a mixture thereof;

(b) phase separating the first product stream into a non-polar hydrophobic liquid stream and a polar non-hydrophobic liquid stream, wherein the polar non-hydrophobic liquid stream comprises water and hydrogen chloride and wherein the non-polar hydrophobic liquid stream comprises the non-polar hydrophobic chlorohydrin esters, and the non-polar hydrophobic carboxylic acid catalyst; and (c) decanting the non-polar hydrophobic liquid stream from the polar non-hydrophobic liquid stream after the phase separating step (b).

2. The process of claim 1 further comprising the steps of:
(d) adding a strong base to the non-polar hydrophobic liquid stream to form a second product stream comprising epoxides, water, and the hydrophobic carboxylic acid catalyst and salts thereof; and
(e) separating the second product stream into a first epoxide stream and a first carboxylic acid/salt stream comprising the hydrophobic carboxylic acid and salts thereof.

3. The process of claim 2 further comprising the steps of:
(f) adding a mineral acid to the first carboxylic acid/salt stream to form a first recovery stream comprising hydrophobic carboxylic acid, and a first discard stream comprising water and a salt;
(g) separating the first recovery stream into a hydrophobic carboxylic acid catalyst component and an aqueous salt component; and
(h) recycling the hydrophobic carboxylic acid catalyst component to the hydrochlorination reactor.

4. The process of claim 2 further comprising the step of:
(i) recycling the first carboxylic acid/salt stream to the hydrochlorination reactor.

5. The process of claim 1 wherein the hydrophobic carboxylic acid is one or more acids selected from the group consisting of benzoic acid, hexanoic acid, heptanoic acid, octanoic acid, oleic acid, stearic acid, terephthalic acid, phenylacetic acid.

6. The process of claim 5 wherein the hydrophobic carboxylic acid is benzoic acid, heptanoic acid or octanoic acid.

7. The process of claim 1 wherein the multihydroxylated aliphatic hydrocarbon is one or more multihydroxylated aliphatic hydrocarbon selected from the group consisting of 1,2-ethanediol; 1,2-propanediol; 1,3-propanediol; 1-chloro-2,3-propanediol; 2-chloro-1,3-propanediol; 1,4-butanediol; 1,5-pentanediol; 1,2-butanediol; 1,2-cyclohexanedimethanol; 1,2,3-propanetriol and mixtures thereof.

8. The process of claim 1 wherein the multihydroxylated aliphatic hydrocarbon is glycerol or one or more glycols, or a mixture thereof.

9. The process of claim 1 wherein the multihydroxylated aliphatic hydrocarbon is obtained from one or more renewable raw materials.

10. The process of claim 1 wherein the hydrogen chloride is aqueous hydrogen chloride; wherein the hydrogen chloride is a hydrogen chloride gas at superatmospheric pressure; or wherein the hydrogen chloride is anhydrous hydrogen chloride.

11. The process of claim 1 wherein the multihydroxylated aliphatic hydrocarbon, multihydroxylated aliphatic hydrocarbon ester, or mixture thereof is obtained from sugar hydrocracking, optionally in a polar solvent; and further wherein the hydrophobic carboxylic acid catalyst is one or more carboxylic acids having a $C_6$-$C_{30}$ substituent group.

12. The process of claim 1 further comprising the steps of:
(j) adding to the non-polar hydrophobic liquid stream one or more multihydroxylated aliphatic hydrocarbons obtained from sugar hydrocracking to selectively remove hydrophobic groups from the hydrophobic chlorohydrin esters to form chlorohydrins;
(k) vaporizing the chlorohydrins leaving a second recovery stream; and
(l) adding at least a part of the second recovery stream to the hydrochlorination reactor.

13. A process for producing a chlorohydrin, an ester of a chlorohydrin, or a mixture thereof comprising:
(A) contacting, in a hydrochlorination reactor, a multihydroxylated aliphatic hydrocarbon, a multihydroxylated aliphatic hydrocarbon ester, or a mixture thereof with a source of hydrogen chloride, in the presence of an extractable carboxylic acid catalyst to produce a reaction solution containing an extractable product stream comprising chlorohydrins, chlorohydrin esters, or a mixture thereof;
(B) adding an extraction medium to the extractable product stream;
(C) extracting into the extraction medium the chlorohydrins, chlorohydrin esters, or mixture thereof;
(D) phase separating the extraction medium from the reaction solution;
(E) decanting the extraction medium containing the chlorohydrins, chlorohydrin esters, or mixture thereof; and
(F) treating the decanted extraction medium by ne or more of the following treatments:
(i) adding a base to the extraction medium to form an epoxide;
(ii) hydrolyzing the extraction medium to liberate chlorohydrins therefrom; or
(iii) adding an alcohol or mixture of alcohols to the extraction medium to form transesters.

14. The process of claim 1 wherein the resultant chlorohydrin, ester of a chlorohydrin, or mixture thereof product obtained by the process contains between 10 wt % and 40 wt % ethylene chlorohydrin hydrophobic ester, between 20 wt % and 80 wt % propylene chlorohydrin hydrophobic ester and, optionally, between 20 wt % and 60 wt % dichlorohydrin hydrophobic ester.

\* \* \* \* \*